(12) United States Patent
Yim et al.

(10) Patent No.: US 7,459,549 B2
(45) Date of Patent: Dec. 2, 2008

(54) COMPOSITION FOR PREPARING NANOPOROUS MATERIAL

(75) Inventors: Jin Heong Yim, Suwon-Si (KR); Byoung Ki Choi, Hwaseong-Si (KR); Duk Keun An, Chuncheon-Si (KR)

(73) Assignee: Samsung Corning Co., Ltd., Gyeonggi-do (KR)

( * ) Notice: Subject to any disclaimer, the term of this patent is extended or adjusted under 35 U.S.C. 154(b) by 555 days.

(21) Appl. No.: 11/002,187

(22) Filed: Dec. 3, 2004

(65) Prior Publication Data

US 2006/0040509 A1    Feb. 23, 2006

(30) Foreign Application Priority Data

Aug. 17, 2004  (KR) .................. 10-2004-0064641

(51) Int. Cl.
  C08B 37/16  (2006.01)
  C08G 77/12  (2006.01)
  C08G 77/18  (2006.01)
  C08G 77/38  (2006.01)

(52) U.S. Cl. ............... 536/103; 528/10; 528/31; 528/33; 977/706; 977/780; 977/781

(58) Field of Classification Search ............ None
See application file for complete search history.

(56) References Cited

U.S. PATENT DOCUMENTS

| | | | |
|---|---|---|---|
| 3,615,272 A | 10/1971 | Cololins et al. | 23/366 |
| 4,399,266 A | 8/1983 | Matsumura et al. | 528/10 |
| 4,999,397 A | 3/1991 | Weiss et al. | 524/755 |
| 5,453,369 A * | 9/1995 | Oguma et al. | 435/193 |
| 5,965,679 A | 10/1999 | Godschalx et al. | 526/281 |
| 6,093,636 A | 7/2000 | Carter et al. | 438/623 |
| 6,107,357 A | 8/2000 | Hawker et al. | 521/77 |
| 6,114,458 A | 9/2000 | Hawker et al. | 525/242 |

OTHER PUBLICATIONS

Shi, X. et al "Cyclodextrin dimer derivatives used as staionary phase . . . " Chromatographia (2000) vol. 52, No. 3/4, pp. 200-204.*
Yi, G. et al "New permethyl-substituted beta-cyclodextrin polysiloxanes . . . " J. Org. Chem. (1993) vol. 58, No. 18, pp. 4844-4850.*
Del Valle, E. "Cyclodextrins and their uses: a review" Proc. Biochem. (2004) vol. 39, pp. 1033-1046.*
Chiu, S. et al "Novel ether-linked secondary face-toface . . . " JOC (2000) vol. 65, No. 9, pp. 2792-2796.*

* cited by examiner

Primary Examiner—Leigh C Maier
(74) Attorney, Agent, or Firm—Harness, Dickey & Pierce, P.L.C.

(57) ABSTRACT

Disclosed herein is a composition for preparing a nanoporous material. The composition comprises i) a cyclodextrin derivative, ii) a thermostable matrix precursor, and iii) a solvent for dissolving the components i) and ii). The composition enables the preparation of a low dielectric constant film in which nanopores with a size of 20 Å or less are uniformly distributed.

11 Claims, 3 Drawing Sheets

COMPOSITION FOR PREPARING NANOPOROUS MATERIAL

BACKGROUND OF THE INVENTION

This non-provisional application claims priority under 35 U.S.C. 119(a) on Korean Patent Application No. 2004-64641 filed on Aug. 17, 2004, which is herein incorporated by reference.

1. Field of the Invention

The present invention relates to a composition for preparing a nanoporous material. More specifically, the present invention relates to a composition for preparing a material in which nanopores with a size of 20Å or less are uniformly distributed, the composition comprising i) a cyclodextrin derivative, ii) a thermostable matrix precursor, and iii) a solvent for dissolving the components i) and ii).

2. Description of the Related Art

Nanoporous materials have drawn attention as materials for adsorbents, supports for catalysts, thermal insulators and electrical insulators in various fields. With the increasing integration of semiconductor devices, the speed between wirings has a significant impact on the performance of the semiconductor devices. Accordingly, an interlayer dielectric film having a low storage capacity is required in order to lower the resistance and capacity between wirings. For this purpose, attempts have been made to use low dielectric constant materials for interlayer dielectric films. For instance, U.S. Pat. Nos. 3,615,272, 4,399,266 and 4,999,397 disclose polysilsesquioxanes having a dielectric constant of about 2.5~3.1 prepared by spin-on deposition ("SOD"), which can replace $SiO_2$ having a dielectric constant of around 4.00 prepared by a conventional chemical vapor deposition (CVD) technique. Further, U.S. Pat. No. 5,965,679 teaches polyphenylenes as organic polymers having a dielectric constant between about 2.65 and about 2.70. However, this dielectric constant range is not sufficiently low to satisfy an increasing demand to fabricate high-speed devices requiring an ultra-low dielectric constant of not higher than 2.50. For this reason, there have been a number of trials to incorporate air having a dielectric constant of 1.0 at the nanometer-scale level into an organic or inorganic material. A method is known for forming a nanoporous silica ($SiO_2$) using tetraethoxysilane ("TEOS") and an appropriate pore-forming agent by a sol-gel process. According to a method taught in U.S. Pat. No. 6,114,458, a lactone-based polymer in a dendrimeric form which can be decomposed at the thin film-forming stage is used as a porogen. A further method for preparing a material having a dielectric constant (K) lower than 3.0 is found in U.S. Pat. Nos. 6,107,357 and 6,093,636. According to this method, first, a particular amount of the lactone-based polymer or a vinyl-based polymer, e.g., polystyrene, polymethacrylate or polyester, in a dendrimeric form is mixed with an organic or inorganic matrix to form a thin film, and is then decomposed at high temperatures to form nano-scale pores.

However, the porous materials prepared by the aforementioned methods have problems that the pores have a size as large as 50 Å~100 Å and are not uniformly distributed in the matrix.

SUMMARY OF THE INVENTION

A feature of the present invention is a cyclodextrin derivative as a novel porogen.

Another feature of the present invention is a composition for preparing a nanoporous material in which nanopores with a size of 20 Å or less are uniformly distributed.

Another feature of the present invention is a method for forming a dielectric film having a very low dielectric constant (κ) of 2.2 or less from the composition.

Another feature of the present invention is a nanoporous structure produced using the composition in which nanopores with a size of 20 Å or less are uniformly distributed.

Still another feature of the present invention a method for utilizing the composition in the manufacture of heat resistant materials, electrical insulators, adsorbents, and supports for catalysts.

In accordance with one aspect of the present invention, the above objects can be accomplished by a novel cyclodextrin derivative.

In accordance with another aspect of the present invention, there is provided a composition for preparing a nanoporous material comprising i) a cyclodextrin derivative, ii) a thermostable matrix precursor, and iii) a solvent for dissolving the components i) and ii).

In accordance with another aspect of the present invention, there is provided a method for forming an interlayer dielectric film for use in a semiconductor device, the method comprising the steps of: coating the composition on a semiconductor substrate by spin coating, dip coating, spray coating, flow coating, or screen printing; evaporating the solvent from the coated substrate; and heating the coated substrate to 150° C.~600° C. under an inert atmosphere or vacuum.

In accordance with another aspect of the present invention, there is provided a nanoporous structure produced using the composition.

In accordance with still another aspect of the present invention, there is provided a method for using the nanoporous structure in the manufacture of heat resistant materials, electrical insulators, adsorbents, and supports for catalysts.

Hereinafter, the present invention will be described in more detail.

The composition for preparing a nanoporous material comprises i) a cyclodextrin derivative, ii) a thermostable matrix precursor, and iii) a solvent for dissolving the components i) and ii).

The thermostable matrix precursor contained in the composition of the present invention may be an inorganic or organic polymer having a glass transition temperature ($T_g$) of at least 400° C.

Examples of the inorganic polymer include (1) silsesquioxanes, (2) condensation products of alkoxysilanes, (3) organic silicates whose composition $RSiO_3$ or $R_2SiO_2$ (wherein R is an organic substituent) is organically modified, and (4) partially condensed orthosilicates having the composition $SiOR_4$ (wherein R is an organic substituent), all of which consist of silicon, carbon, oxygen, and hydrogen.

The silsesquioxanes derived from organic polysiloxanes can be exemplified by hydrogen silsesquioxane, alkyl silsesquioxanes, aryl silsesquioxanes, and copolymers of these silsesquioxanes. Examples of alkyl silsesquioxanes include, but are not limited to, methyl silsesquioxane, ethyl silsesquioxane, and propyl silsesquioxane. Examples of aryl silsesquioxanes, but are not limited to, phenyl silsesquioxane. As copolymers of these silsesquioxanes, there may be used, without limitation, copolymers of hydrogen silsesquioxane and phenyl silsesquioxane, copolymers of methyl silsesquioxane and ethyl silsesquioxane, and copolymers of methyl silsesquioxane and vinyl silsesquioxane.

The condensation products of alkoxysilanes refer to materials that alkoxysilanes are partially condensed so as to have a number-average molecular weight of 50~20,000. As such alkoxysilanes, there may be mentioned, for example, tetraethoxysilane, and tetramethoxysilane.

In the composition $RSiO_3$ or $R_2SiO_2$ of the organic silicates, the substituent R may be an alkyl group, such as methyl, ethyl, and propyl.

In the composition $SiOR_4$ of the orthosilicates, the substituent R may be an alkyl group, such as methyl, ethyl, and propyl.

In addition, as the thermostable organic matrix precursor, there can be used an organic polymer that are cured at high temperatures to form a stable reticular structure. Non-limiting examples of the organic polymer include polyimide-based polymers which can undergo imidization, such as poly(amic acid), poly(amic acid ester), etc; polybenzocyclobutene-based polymers; and polyarylene-based polymers, such as polyphenylene, poly(arylene ether), etc.

The matrix precursor is more preferably a highly soluble organic polysiloxane-based resin having a silanol group (Si—OH) content of at least 10 mole %, preferably at least 25 mole %, which is prepared through hydrolysis and condensation of a cyclic siloxane monomer alone or a mixture with another cyclic siloxane monomer in the presence of an appropriate catalyst, or through hydrolysis and condensation of a cyclic siloxane monomers and optionally a silane-based monomer. Only when the Si—OH content is at least 10 mole %, the composition of the present invention shows not only satisfactory mechanical strength, but also good compatibility with the cyclodextrin derivative.

The cyclic siloxane monomer used to prepare the matrix precursor is a compound wherein silicon atoms are linked to each other via oxygen atoms to form a cyclic structure, and the end of each branch contains organic groups constituting a hydrolyzable substituent. The cyclic siloxane monomer can be represented by Formula 1 below:

Formula 1 wherein $R_1$ is a hydrogen atom, a $C_{1\sim3}$ alkyl group, or a $C_{6\sim15}$ aryl group; $X_1$, $X_2$ and $X_3$ are independently a hydrogen atom, a $C_{1\sim3}$ alkyl group, a $C_{1\sim10}$ alkoxy group, or a halogen atom, at least one of these substituents being a hydrolyzable functional group; m is an integer ranging from 0 to 10; and p is an integer ranging from 3 to 8;

or Formula 2 below:

Formula 2 wherein $R_1$ is a hydrogen atom, a $C_{1\sim3}$ alkyl group, or a $C_{6\sim15}$ aryl group; $R_2$ is a hydrogen atom, a $C_{1\sim10}$ alkyl group, or $SiX_1X_2X_3$ (in which $X_1$, $X_2$ and $X_3$ are independently a hydrogen atom, a $C_{1\sim3}$ alkyl group, a $C_{1\sim10}$ alkoxy group, or a halogen atom); and p is an integer between 3 and 8.

The method for preparing the cyclic siloxane monomers is not specifically limited, but hydrosililation reaction using a metal catalyst is preferred.

As suitable cyclic siloxane monomers, commercially available siloxane monomers whose terminal functional groups are halogen atoms can be used as it is or, if necessary, after converting the terminal halogen atoms into alkyl or alkoxy groups. Such a conversion method is not specifically limited, as long as it does not inhibit the object of the present invention, and may be one of any previously known methods in the art. For example, conversion of terminal halogen atoms into alkoxy groups can be carried out by reacting the siloxane monomers with alcohol and triethylamine.

Specifically, the cyclic siloxane monomer may be a monomer represented by Formula 3 below:

Formula 3 or a monomer represented by Formula 3 below:

Formula 4

The compound of Formula 3 corresponds to that of Formula 1 wherein $R_1$ is a methyl group, $X_1$, $X_2$ and $X_3$ all are a methoxy group, m is 1, and p is 4. The compound of Formula 4 corresponds to that of Formula 2 wherein $R_1$ is a methyl group, $R_2$ is Si $(OCH_3)$, and p is 4.

The silane-based monomer used in the preparation of the matrix precursor contains organic groups that form a hydrolyzable substituent at the end of each branch, and can be represented by Formula 5 below:

$$RSiX_1X_2X_3 \quad \text{Formula 5}$$

wherein R is a hydrogen atom, a $C_{1~3}$ alkyl group, a $C_{3~10}$ cycloalkyl group, a $C_{1~10}$ alkoxy group, or $C_{6~15}$ aryl group; and $X_1$, $X_2$ and $X_3$ are independently a $C_{1~3}$ alkyl group, a $C_{1~10}$ alkoxy group, or a halogen atom.

Specific examples of the silane-based monomer include, but are not limited to, phenyltrimethoxysilane, tetramethoxysilane, and methyltrimethoxysilane, which is represented by Formula 6 below:

Formula 6

In view of the objects of the present invention, it is more preferred that the monomer of Formula 3 and the monomer of Formula 6 are used in a molar ratio ranging from 0.01:0.99 to 0.99:0.01, or the monomer of Formula 4 and the monomer of Formula 6 are used in a molar ratio ranging from 0.01:0.99 to 0.99:0.01 to prepare the matrix precursor used in the present invention.

Conditions for the hydrolysis and condensation are as follows. The acid catalyst used herein is not specifically limited, but is preferably hydrochloric acid, benzenesulfonic acid, oxalic acid, nitric acid, formic acid, or a mixture thereof. The equivalence ratio of the water used during the hydrolysis and condensation to reactive groups present in the monomers is in the range of 1.0~100.0:1, and preferably 1.0~10.0:1.

The reaction is carried out at 0° C.~200° C., preferably 50~110° C. for 1~100 hrs, and more preferably 5~48 hrs.

The composition of the present invention comprises, as a porogen, a cyclodextrin derivative represented by Formula 7 below:

Formula 7 wherein n is an integer of 3 or more; $R_1$ is a substituent containing OH, SH, or $NH_2$; and $R_2$ and $R_3$ are independently —$OR_4$ [in which $R_4$ is a $C_{2~30}$ acyl group, a $C_{1~20}$ alkyl group, a $C_{3~10}$ cycloalkyl group, a $C_{1~20}$ hydroxyalkyl group, a carboxyl group, or a silicon compound represented by $Sir_1r_2r_3$ (in which $r_1$, $r_2$ and $r_3$ are independently a $C_{1~5}$ alkyl group, a $C_{1~5}$ alkoxy group, or a $C_{6~20}$ aryl group)]; or

$R_2$ and $R_3$ are independently a substituent containing OH, SH, or $NH_2$; and $R_1$ is —$OR_4$ [in which $R_4$ is a $C_{2~30}$ acyl group, a $C_{1~20}$ alkyl group, a $C_{3~10}$ cycloalkyl group, a $C_{1~20}$ hydroxyalkyl group, a carboxyl group, or a silicon compound represented by $Sir_1r_2r_3$ (in which $r_1$, $r_2$ and $r_3$ are independently a $C_{1~5}$ alkyl group, a $C_{1~5}$ alkoxy group, or a $C_{6~20}$ aryl group)].

Introduction of a reactive group, particularly sulfur-containing one, into the cyclodextrin derivative enables applicability to various fields. For example, when the cyclodextrin derivative contains a tiol group (—SH), it can be self-assembled to the surface of metal to form a monolayer, and two molecules of the cyclodextrin derivative can form a molecular structure in a duplex configuration by the action of a catalyst, such as iodide atom (I). Some examples of the molecular structure are shown in Formula 8 below:

Formula 8 wherein n is an integer of from 3 to 10; $R_1'$ and $R_2'$ are independently a divalent group derived from substituents containing OH, SH or $NH_2$ which can form a crosslinked structure, the specific examples including, without limitation, —S—S—, —COO—$(CH_2)_m$—COO— and —N—$(CH_2)_m$—N—; and $R_3$ is —$OR_4$ [in which $R_4$ is a $C_{2~30}$ acyl group, a $C_{1~20}$ alkyl group, a $C_{3~10}$ cycloalkyl group, a $C_{1~20}$ hydroxyalkyl group, a carboxyl group, or a silicon compound represented by $Sir_1r_2r_3$ (in which $r_1$, $r_2$ and $r_3$ are independently a $C_{1~5}$ alkyl group, a $C_{1~5}$ alkoxy group, or a $C_{6~20}$ aryl group)];
and Formula 9 below:

Formula 9 wherein n is an integer of from 3 to 10; $R_3'$ is a divalent group derived from substituents containing OH, SH or $NH_2$ which can form a crosslinked structure, the specific examples including, without limitation, —S—S—, —COO—$(CH_2)_m$—COO— and —N—$(CH_2)_m$—N—; and $R_1$ and $R_2$ are independently —$OR_4$ [in which $R_4$ is a $C_{2~30}$ acyl group, a $C_{1~20}$ alkyl group, a $C_{3~10}$ cycloalkyl group, a $C_{1~20}$ hydroxyalkyl group, a carboxyl group, or a silicon compound represented by $Sir_1r_2r_3$ (in which $r_1$, $r_2$ and $r_3$ are independently a $C_{1~5}$ alkyl group, a $C_{1~5}$ alkoxy group, or a $C_{6~20}$ aryl group)].

Since two molecules constituting a duplex configuration have a similar diameter and height, they are symmetrically arranged. Based on this characteristic, the duplex configuration is available in various applications, such as organic nanoparticles and nanocarriers.

Cyclodextrin derivatives used in the present invention can be used alone, but can be reacted with each other to prepare a compound in a duplex configuration, e.g., the compound of Formula 8 or 9.

Non-limiting examples of porogens used in the present invention include, but are not limited to, compounds represented by formulae 10 to 12 below:

Formula 10 wherein AcS represents acyl sulfide;

; and

Formula 11

Formula 12

Specifically, the porogens of Formulae 10 and 11 can be prepared by Reaction Scheme 1 below.

Reaction Scheme 1

On the other hand, the cyclodextrin derivative of Formula 12 has a molecular structure in which two molecules of the cyclodextrin derivative form a duplex configuration, and can be easily prepared by Reaction Scheme 2 below.

Reaction Scheme 2

These synthetic pathways will be described in greater detail in the Examples section that follows.

Since even a small amount of the porogen can form a sufficiently large number of pores, the porogen can be applied to various thin-film formation processes, and at the same time, enables formation of thin films having superior mechanical properties relative to the same dielectric constant by designing an optimized porous structure. Specifically, the porogen used in the present invention is prepared by a unimolecular template approach. According to this approach, the hydrophobic moiety of the molecules is positioned inside and the hydrophilic moiety of the molecules is positioned outside to form pores having a size of 2 nm or less, controlling functional groups of the derivative is simple, and the stability of the pores is superior. In addition, the cyclodextrin-based porogen used in the present invention increases the molecular volume, and decreases the number of functional groups per unit volume, thus preventing the pores from being collapsed.

The composition of the present invention is prepared by dissolving the thermostable matrix precursor and the thermally unstable cyclodextrin-based porogen in an appropriate solvent. The content of the cyclodextrin derivative is in the range of 0.1%~95% by weight, and preferably 10%~70% by weight, based on the total solid content (i.e. the sum of the amounts of the cyclodextrin derivative and the matrix precursor) of the composition according to the present invention. When the content of the cyclodextrin derivative is less than 0.1% by weight, pore-forming effects are negligible. On the other hand, when the content of the cyclodextrin derivative exceeds 95% by weight, the mechanical strength of the matrix precursor is poor.

Examples of the solvent used include, but are not limited to, aromatic hydrocarbons, such as anisole, xylene, and mesitylene; ketones, such as methyl isobutyl ketone, 1-methyl-2-pyrrolidinone, and acetone; ethers, such as tetrahydrofuran, and isopropyl ether; acetates, such as ethyl acetate, butyl acetate, and propylene glycol methyl ether acetate; amides, such as dimethylacetamide, and dimethylformamide; γ-butyolactone; alcohols, such as isopropyl alcohol, butyl alcohol, and octyl alcohol; silicon solvents; and mixtures thereof.

The solvent should be used in an amount sufficient to dissolve the matrix precursor up to a concentration required for application on a substrate, and may be present in the range of 20%~99.9% by weight, and preferably 70%~95% by weight in the composition. When the solvent is used in an amount of less than 20% by weight, it cannot completely dissolve the precursor. Meanwhile, when the solvent is used in an amount exceeding 99.9% by weight, there is a problem that a thin film to be formed has a thickness of 1,000 Å or less.

The present invention is also directed to a method for forming an interlayer dielectric film for use in a semiconductor device by applying the composition to a substrate to form a nanoporous thin film. The method of the present invention will be specifically explained below.

First, the composition of the present invention is applied on a substrate by spin coating, dip coating, spray coating, flow coating, screen printing, or so on. The application is preferably carried out by spin coating at a speed of 1,000~5,000 rpm. After coating, the organic solvent is evaporated from the coated substrate to deposit a resinous film on the substrate. The evaporation may be carried out by exposing the coated substrate to atmosphere (simple air-drying), subjecting the substrate to vacuum conditions at the initial stage of the subsequent curing step, or mild heating at 100° C. or lower.

The resulting coating film may be cured by heating it at a temperature of 150° C.~600° C., preferably 200° C.~450° C. wherein pyrolysis of the cyclodextrin derivative occurs, thereby providing a crack-free insoluble film. As used herein, by "crack-free film" is meant a film without any crack when observed under an optical microscope at a magnification of 1,000×. As used herein, by "insoluble film" is meant a film which is substantially insoluble in any solvent described as being useful for the coating and deposition of the siloxane-based resin. The heat-curing of the coating film may be performed under an inert gas (nitrogen, argon, etc.) atmosphere or vacuum conditions for 10 hrs, and preferably 30 min. to 1 hr.

Following the curing, fine pores with a size of about 20 Å or less are formed in the matrix, leading to a thin film having a low dielectric constant ($\kappa \leq 2.5$). Moreover, a thin film having an ultra-low dielectric constant ($\kappa \leq 2.2$), which is useful as an interlayer dielectric film for use in a semiconductor device, can be formed by appropriately controlling the content of the matrix precursor and the cyclodextrin derivative.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

The present invention will now be described in more detail with reference to the following preferred examples. However, these examples are given for the purpose of illustration and are not to be construed as limiting the scope of the invention.

EXAMPLE 1

Synthesis of Matrix Monomers

EXAMPLE 1-1

Synthesis of Monomer "a"

To a flask were added 29.014 mmol (10.0 g) of 2,4,6,8-tetramthyl-2,4,6,8-tetravinylcyclotetrasiloxane and a solution of 0.164 g of platinum(0)-1,3-divinyl-1,1,3,3-tetramethyldisiloxane complex in xylenes, and then diluted in 300 ml of diethyl ether. After the reaction solution was cooled to $-78°$ C., 127.66 mmol (17.29 g) of trichlorosilane was slowly added thereto. The reaction temperature was gradually raised to room temperature. At this temperature, the reaction was continued for 40 hours. The reaction solution was concentrated at a reduced pressure (~0.1 torr) to completely remove volatile substances, and then 100 ml of hexane was added to the concentrate. The resulting mixture was stirred for 1 hour and filtered through celite to obtain a colorless clear solution. The hexane was evaporated at a reduced pressure (~0.1 torr) to obtain a reaction product as a liquid.

Next, 11.56 mmol (10.0 g) of the reaction product was diluted in 50 ml of tetrahydrofuran (THF), and then 138.71 mmol (13.83 g) of triethylamine was added thereto. After the solution was cooled to $-78°$ C., 136.71 mmol (4.38 g) of methyl alcohol was slowly added thereto. The reaction temperature was gradually raised to room temperature. At this temperature, the reaction was continued for 15 hours. The reaction solution was filtered through celite, and then the filtrate was concentrated at a reduced pressure (about 0.1 torr) to completely remove volatile substances. 100 ml of hexane was added to the concentrate. The resulting mixture was stirred for 1 hour and filtered through celite. After 5 g of activated charcoal was added to the obtained filtrate, the mixture was stirred for 10 hours and filtered through celite. The obtained filtrate was concentrated at a reduced pressure (~0.1 torr) to remove the hexane, affording colorless monomer "a" represented by the following formula:

The analytical results of the $^1$H-NMR spectrum (300 MHz) of the monomer "a" are as follows: δ 0.09 (s, 12H, 4×[—CH$_3$]), 0.52~0.64 (m, 16H, 4×[—CH$_2$CH$_2$—]), 3.58 (s, 36H, 4×[—OCH$_3$]$_3$).

EXAMPLE 1-2

Synthesis of Monomer "b"

A solution of 21.4 mmol (3.8 g) of palladium (II) dichloride [PdCl$_2$(II)] in 50 ml of carbon tetrachloride was placed in a flask, and then 41.6 mmole (10.00 g) of 2,4,6,8-tetramethyl-2,4,6,8-cyclotetrasiloxane was slowly added thereto. The mixture was allowed to react at room temperature for about 10 minutes. The reaction mixture was filtered through celite and MgSO$_4$. Thereafter, the obtained filtrate was diluted in 200 ml of tetrahydrofuran, and then 183.0 mmol (18.5 g) of triethylamine was added thereto. The resulting mixture was stirred at room temperature for 10 minutes, and then an excess of methyl alcohol (366.1 mmol (11.7 g)) was added thereto. The resulting mixture was reacted for 5 hours. The reaction solution was filtered through celite, and the filtrate was concentrated at a reduced pressure (~0.1 torr) to remove volatile substances, affording monomer "b" represented by the following formula:

The analytical results of the ¹H-NMR spectrum (300 MHz) of the monomer "b" are as follows: δ 0.067 (s, 12H, 4×[—CH₃]), 3.55 (s, 12H, 4×[—OCH₃]).

EXAMPLE 2

Preparation of Matrix Precursors

Precursor A: Copolymerization of Monomer "a" and Methyltrimethoxysilane (MTMS)

After 37.86 mmol (5.158 g) of methyltrimethoxysilane and 3.79 mmol (3.162 g) of the monomer "a" prepared in Example 1-1 were charged into a flask, the mixture was diluted in 100 ml of tetrahydrofuran. Separately, water and concentrated hydrochloric acid (containing 35% hydrogen chloride) were mixed in a ratio of 100:0.12 (v/v) to prepare a hydrochloric acid in which the hydrogen chloride was present in an amount of 0.0159 mmol. The hydrochloric acid was slowly added to the previous mixture, and then water was slowly added thereto until the total amount of water, including water contained in the hydrochloric acid, reached 529.67 mmol (9.534 g). The reaction temperature was gradually increased to 70° C. At this temperature, the reaction was continued for 16 hours. The reaction solution was transferred to a separatory funnel, and then 100 ml of diethyl ether was added thereto, followed by washing with water (100 ml×5) and addition of anhydrous sodium sulfate (5 g). The resulting mixture was stirred at room temperature for 10 hours to remove a small quantity of water that remained, and filtered to obtain a colorless clear solution. The solution was concentrated at a reduced pressure (about 0.1 torr) to remove volatile substances, affording 5.5 g of matrix precursor "A" as a white powder. The contents (%) of Si—OH, Si—OCH₃ and Si—CH₃ in the precursor were determined through ¹H-NMR analysis. Specifically, the contents was obtained by substituting the areas under the characteristic peaks into the following Equations 1 through 3 below:

Si—OH (%)=Area(Si—OH)÷[Area(Si—OH)+Area(Si—OCH₃)/3+Area(Si—CH₃)/3]×100   [Equation 1]

Si—OCH₃ (%)=Area(Si—OCH₃)/3÷[Area(Si—OH)+Area(Si—OCH₃)/3+Area(Si—CH₃)/3]×100   [Equation 2]

Si—CH₃ (%)=Area(Si—CH₃)/3÷[Area(Si—OH)+Area(Si—OCH₃)/3+Area(Si—CH₃)/3]×100   [Equation 3]

As a result, the contents of Si—OH (%), Si—OCH₃ and Si—CH₃ in the precursor "A" were 24.60%, 0.82%, and 74.6%, respectively. The precursor "A" was analyzed for molecular weight and molecular weight distribution by gel permeation chromatography (Waters Co.). As a result, the molecular weight of the precursor "A" was 3,620, and the molecular weight distribution was 1.936.

Precursors "B" and "C": Copolymerization of monomer "b" and methyltrimethoxysilane Precursors "B" and "C" were prepared in the same manner as in the preparation of precursor "A" above, except that methyltrimethoxysilane and monomer "b" were used in amounts indicated in Table 1 below. The amounts of the monomer used, and the contents of Si—OH, Si—OCH₃ and Si—CH₃ in the precursors are shown in Table 1. The molecular weight of precursor B was 1,450, and the molecular weight distribution was 1.408. The molecular weight of precursor C was 2,930, and the molecular weight distribution was 2.139.

TABLE 1

| Precursors | Monomers (mol) | | HCl (ml) | H₂O (ml) | Amount of obtained polymer (g) | Si—OH (%) | Si—OCH₃ (%) | Si—CH₃ (%) |
| --- | --- | --- | --- | --- | --- | --- | --- | --- |
| | Monomer "b" | MTMS | | | | | | |
| B | 0.41 | 1.62 | 8.1 | 584.3 | 111 | 33.2 | 0.6 | 66.2 |
| C | 0.42 | 0.98 | 6.7 | 319.2 | 134 | 32.2 | 0.8 | 57.5 |

EXAMPLE 3

Synthesis of Cyclodextrin-Based Porogens

EXAMPLE 3-1

Synthesis of heptakis(6-S-acetyl-2,6-di-O-methyl)-β-cyclodextrin 8.81 mmol (10.0 g) of β-cyclodextrin hydrate was heated at a reduced pressure (~0.1 torr) and 100° C. for 3 hours to remove water, and was then diluted in 150 ml of pyridine. The temperature was cooled to 0° C. To the mixture was slowly added a solution of 73.0 mmol (11 g) of tert-butyldimethylsilyl chloride (TBSCl) in 50 ml of pyridine. The resulting reaction mixture was stirred for 3 hours. After the reaction temperature was gradually raised to room temperature, the reaction was allowed to proceed for 24 hours. Cooling water was added to the reaction mixture to obtain precipitates. The obtained precipitates was carefully filtered under suction, and then washed with distilled water to obtain a white crystal. The crystal was heated to 100° C. at a reduced pressure (~0.1 torr) for 3 hours to remove the remaining water, giving a reaction product as a solid.

10.0 g of the reaction product was slowly added to a solution of 10.0 g of sodium hydride (NaH, in 60% mineral oil) in 150 ml of tetrahydrofuran (THF) at −78° C. After the reaction temperature was gradually raised to room temperature, the reaction was continued for 2 hours. Thereafter, the temperature was cooled to 0° C. After 0.37 moles (23 ml) of iodomethane (MeI) was slowly added, the reaction temperature was gradually raised to room temperature, at which the reaction was allowed to proceed for 24 hours. 100 ml of methanol was added to the reaction mixture, and the resulting mixture was concentrated at a reduced pressure (~0.1 torr) to remove volatile substances. The concentrate was diluted in 100 ml of water, and then extraction was carried out using methylene chloride (MC) (200 ml×2). The extracted solution was concentrated at a reduced pressure (~0.1 torr) to remove volatile substances. The concentrate was loaded onto a column packed with silica gel (70-230 mesh, Merck), and the column was then eluted with a mixed solvent of diethyl ether and hexane (1:5) to afford heptakis(6-O-tert-butyldimethylsilyl-2,6-di-O-methyl)-β-cyclodextrin).

4.70 mmol (10.0 g) of heptakis(6-O-tert-butyldimethylsilyl-2,6-di-O-methyl)-β-cyclodextrin) was diluted in 150 ml of tetrahydrofuran (THF), and then 50 ml of tetrabutyl ammonium chloride (TBAF, 1.0M in THF) was slowly added thereto. After the resulting mixture was refluxed for 3 hours with stirring, it was concentrated at a reduced pressure (~0.1 torr) to remove volatile substances, giving a reaction product as an oil.

The reaction product was diluted in 50 ml of pyridine, and then 50 ml of acetic anhydride was slowly added thereto at 0° C. After the reaction temperature was gradually raised to 100° C., the reaction was allowed to proceed for 2 hours. The reaction mixture was concentrated at a reduced pressure (~0.1 torr) to remove the pyridine. The concentrate was diluted in 100 ml of water, and extraction was carried out using methylene chloride (20 ml×2). The extracted solution was concentrated at a reduced pressure (~0.1 torr) to remove volatile substances. The concentrate was loaded onto a column packed with silica gel (70-230 mesh, Merck), and the column was then eluted with a mixed solvent of ethyl acetate (EA) and methanol (10:1) to afford heptakis(6-O-acetyl-2,6-di-O-methyl)-β-cyclodextrin).

6.15 mmol (10.0 g) of the heptakis(6-O-acetyl-2,6-di-O-methyl)-β-cyclodextrin) was diluted in 200 ml of methanol, and then 10.0 mmol (0.54 g) of sodium methoxide (NaOCH$_3$) was slowly added thereto. The resulting mixture was stirred at room temperature for 3 hours. 10 g of an acidic ion exchange resin (Amberlite IR-120 (Aldrich)) was added to neutralize the reaction mixture, and filtered off under suction. Concentration was carried out at a reduced pressure (~0.1 torr) to remove the methanol, giving a reaction product as a solid. The reaction product was dissolved in methylene chloride (MC) in smallest amount, and then a large amount of hexane was slowly added thereto to recrystallize the solution. The crystal thus formed was carefully filtered, and washed with hexane to afford heptakis(2,3-di-O-methyl)-β-cyclodextrin.

7.51 mmol (10.0 g) of the heptakis(2,3-di-O-methyl)-β-cyclodextrin was diluted in 100 ml of pyridine, and then 15 ml of methane sulfonyl chloride (MsCl) was slowly added thereto at −10° C. The resulting mixture was stirred for 10 minutes. After the temperature was raised to room temperature, the mixture was allowed to react for 12 hours. The reaction mixture was concentrated at a reduced pressure (~0.1 torr) to remove the pyridine. The concentrate was diluted in 100 ml of water, and extraction was carried out using methylene chloride (MC) (200 ml×2). The extracted solution was neutralized using 100 ml of aqueous sodium hydrogen carbonate solution, and was then concentrated at a reduced pressure (~0.1 torr) to remove volatile substances, giving a reaction product as an oil.

The reaction product was diluted in 200 ml of N,N-dimethylformamide (DMF), and 30 g of potassium thioacetate (KSAc) was slowly added thereto at room temperature. The resulting mixture was allowed to react for 24 hours. The reaction mixture was concentrated at a reduced pressure (~0.1 torr) to remove the N,N-dimethylformamide (DMF). The concentrate was loaded onto a column packed with silica gel (70-230 mesh, Merck), and the column was then eluted with a mixed solvent of ethyl acetate (EA) and methanol (10:1) to afford a reaction product as a solid. 10 g of activated charcoal was added to the reaction product, and the resulting mixture was stirred for 1 hour. The mixture was filtered through celite, and then the filtrate was concentrated at a reduced pressure (~0.1 torr) to remove volatile substances, affording heptakis (6-S-acetyl-2,6-di-O-methyl)-β-cyclodextrin [hereinafter, referred to as 'porogen 1'] as a colorless solid, represented by the following Formula:

The analytical results of the $^1$H-NMR spectrum (300 MHz, CDCl$_3$) of the porogen are as follows: δ 2.36 (s, 21H, 7×[OCOCH$_3$]), 3.50, 3.62 (2 s, each 21H, 7×[—OCH$_3$]), 5.07 (d, 7H, 7×H-1).

EXAMPLE 3-2

Synthesis of heptakis(6-thionyl-2,3-di-O-methyl)-β-cyclodextrin 5.76 mmol (10.0 g) of heptakis(6-S-acetyl-2,6-di-O-methyl)-β-cyclodextrin was diluted in 200 ml of methanol, and then 750 ml of sodium methoxide (NaOCH$_3$, 0.1N in MeOH) was slowly added thereto at 0° C. The resulting mixture was stirred for 1 hour. After the temperature was gradually raised to room temperature, the mixture was allowed to react for 12 hours. 10 g of an acidic ion exchange resin (Amberlite IR-120 (Aldrich)) was added to neutralize the reaction mixture, and filtered off under suction. Concentration was carried out at a reduced pressure (~0.1 torr) to remove the methanol, giving a reaction product as a solid. The reaction product was dissolved in 100 ml of brine (NaCl) solution and then extraction was carried out using methylene chloride (MC) (200 ml×2). 10 g of activated charcoal was added to the extracted solution, and the resulting mixture was stirred for 1 hour. The mixture was filtered through celite. The obtained filtrate was concentrated at a reduced pressure (~0.1 torr) to remove volatile substances, affording heptakis(6-thionyl-2,3-di-O-methyl)-β-cyclodextrin) [hereinafter, referred to as 'porogen 2'] as a light yellow solid, represented by the following Formula:

The analytical results of the $^1$H-NMR spectrum (300 MHz, CDCl$_3$) of the porogen are as follows: δ 3.53, 3.65 (2s, each 21H, 7×[—OCH$_3$]), 5.13 (d, 7H, 7×H-1).

EXAMPLE 3-3

Synthesis of Duplex beta-cyclodextrin Compound 1.3 mmol (1.875 g) of the heptakis(6-thionyl-2,3-di-O-methyl)-β-cyclodextrin prepared in Example 3-2 was dissolved in 200 ml of methylene chloride (MC). While stirring the solution at room temperature, 4.3 mmol (43 ml) of 0.1N I$_2$ solution was slowly added over 3 hours to allow to react with each other. The reaction mixture was further stirred at room temperature for 3 hours. In the same manner, 3.9 mmol (25 ml) of 0.1N I$_2$ solution was slowly added to the reaction mixture. The resulting mixture was stirred at room temperature for 3 hours. The mixture was washed with distilled water (×2), and was then washed with 1.0N aqueous sodium hydrogen carbonate solution and distilled water twice, respectively. The remaining water was removed using sodium sulfate as a desiccant, and then volatile substances were removed by concentration at a reduced pressure (~0.1 torr). The concentrate was loaded onto a column packed with silica gel (70-230 mesh, Merck), and the column was then eluted with a mixed solvent of ethyl acetate (EA) and methanol (10:1) to afford 1.15 g of a duplex-β-cyclodextrin [hereinafter, referred to as 'porogen 3'] as a light yellow solid, represented by the following Formula:

The analytical results of the $^1$H-NMR spectrum (300 MHz, CDCl$_3$) of the porogen are as follows: δ 3.52, 3.62 (2s, each 21H, 7×[—OCH$_3$]), 5.05 (d, 7H, 7×H-1).

EXAMPLE 4

Formation of Nanoporous Thin Films, and Measurement of Thickness and Refractive Index of the Thin Films The siloxane-based resin matrix precursors prepared in Example 2, the cyclodextrin compounds prepared in Example 3, and propylene glycol methyl ether acetate were mixed together in accordance with the particular ratios as described in Table 2 below to prepare corresponding compositions according to the present invention. For comparison, compositions were prepared by using tCD(heptakis (2,3,6-tri-O-methyl)-β-cyclodextrin), instead of the cyclodextrin compounds prepared in Example 3, in accordance with the particular ratios as described in Table 3 (Comparative Examples). The solid content indicated in Table 2 refers to a weight percentage of the corresponding siloxane-based resinous matrix precursor and cyclodextrin compound, relative to the total weight of the composition (i.e., siloxane resinous matrix precursor+cyclodextrin compound+propylene glycol methyl ether acetate). The porogen content represents a weight percentage of the corresponding cyclodextrin derivative in the solid content.

TABLE 2

| Example No. | Solid content (precursor + porogen), wt % | Kind of precursors | Porogens Kind | Content (wt %) |
|---|---|---|---|---|
| Ex. 1-1 | 30 | A | Porogen 1 | 10 |
| Ex. 1-2 | 30 | A | Porogen 1 | 30 |
| Ex. 1-3 | 30 | A | Porogen 1 | 50 |
| Ex. 2-1 | 30 | A | Porogen 2 | 10 |
| Ex. 2-2 | 30 | A | Porogen 2 | 20 |
| Ex. 2-3 | 30 | A | Porogen 2 | 30 |
| Ex. 2-4 | 30 | A | Porogen 2 | 40 |
| Ex. 2-5 | 30 | A | Porogen 2 | 50 |
| Ex. 3-1 | 30 | A | Porogen 3 | 10 |
| Ex. 3-2 | 30 | A | Porogen 3 | 20 |
| Ex. 3-3 | 30 | A | Porogen 3 | 30 |
| Ex. 4-1 | 32 | B | Porogen 2 | 10 |
| Ex. 4-2 | 32 | B | Porogen 2 | 20 |
| Ex. 4-3 | 32 | B | Porogen 2 | 30 |
| Ex. 4-4 | 32 | B | Porogen 2 | 40 |
| Ex. 4-5 | 32 | B | Porogen 2 | 50 |
| Ex. 5-1 | 32 | C | Porogen 1 | 10 |
| Ex. 5-2 | 32 | C | Porogen 1 | 30 |
| Ex. 5-3 | 32 | C | Porogen 1 | 50 |
| Ex. 6-1 | 32 | C | Porogen 3 | 10 |
| Ex. 6-2 | 32 | C | Porogen 3 | 20 |
| Ex. 6-3 | 32 | C | Porogen 3 | 30 |

TABLE 3

| Example No. | Solid content (precursor + porogen), wt % | Kind of precursors | Porogens Kind | Content (wt %) |
|---|---|---|---|---|
| Comp. Ex. 1 | 30 | A | — | — |
| Comp. Ex. 2-1 | 30 | A | tCD | 10 |
| Comp. Ex. 2-2 | 30 | A | tCD | 20 |
| Comp. Ex. 2-3 | 30 | A | tCD | 30 |
| Comp. Ex. 2-4 | 30 | A | tCD | 40 |
| Comp. Ex. 2-5 | 30 | A | tCD | 50 |
| Comp. Ex. 3 | 32 | B | — | — |
| Comp. Ex. 4-1 | 32 | B | tCD | 10 |
| Comp. Ex. 4-2 | 32 | B | tCD | 20 |
| Comp. Ex. 4-3 | 32 | B | tCD | 30 |
| Comp. Ex. 4-4 | 32 | B | tCD | 40 |
| Comp. Ex. 4-5 | 32 | B | tCD | 50 |

These compositions were spin-coated onto different boron-doped p-type silicon wafers at 3,000 rpm. After the wafers were then placed on a hot plate at 120° C. for 3 minutes, they were subjected to a series of soft baking at 150° C. for 1 minute and at 250° C. for 1 minute to completely remove organic solvents. The baked substrates were cured in a Linberg furnace under vacuum at 420° C. for 60 minutes to form low dielectric constant films.

The thickness and refractive index of the dielectric films were measured using a prism coupler. The results are shown in Tables 4 and 5.

EXAMPLE 5

Measurement of Dielectric Constant and Physical Properties

The dielectric constant of the thin films formed in Example 4 was measured in accordance with the following procedure. First, MIM (metal-insulator-metal)-structured test pieces were produced using the thin films. The dielectric constant was measured around 100 kHz using an LCR METER (HP4284A) accompanied with a probe station. The modulus and hardness, which are indicative of physical properties of the thin films, were determined by a continuous stiffness measurement (CSM) using a nanoindenter II (MTS). The results are summarized in Tables 4 and 5.

Figure 1:
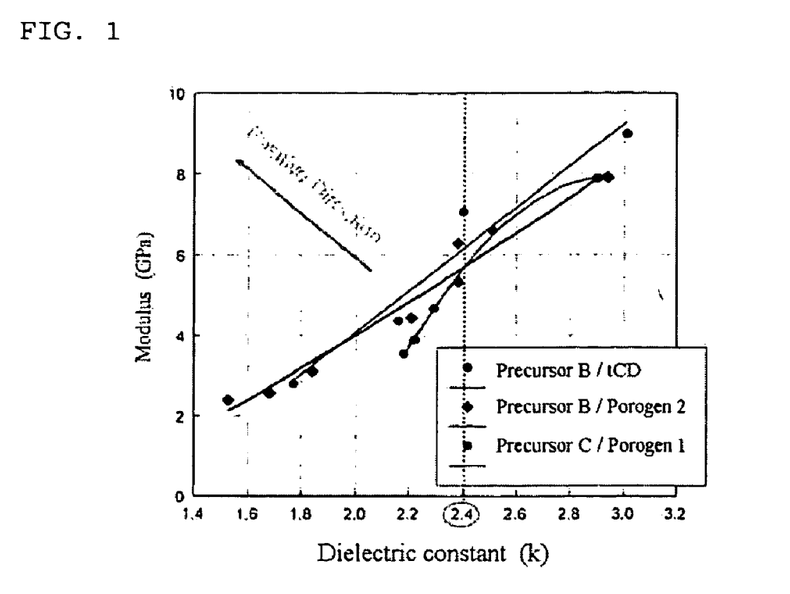
FIG. 1 is a graph showing the relation between the dielectric constant and the modulus of some thin films formed in Example 4 of the present invention.

FIG. 1 is a graph showing the relation between the dielectric constant and the modulus of some thin films formed in Example 4. As apparent from the results shown in the graph of FIG. 1, it has been confirmed that the modulus of the thin films formed using the compositions of the present invention is higher than that of the thin films formed using the compositions of Comparative Examples, particularly at a dielectric constant lower than 2.4.

EXAMPLE 6

Observation of Nanopores in Thin Films

Figure 2:
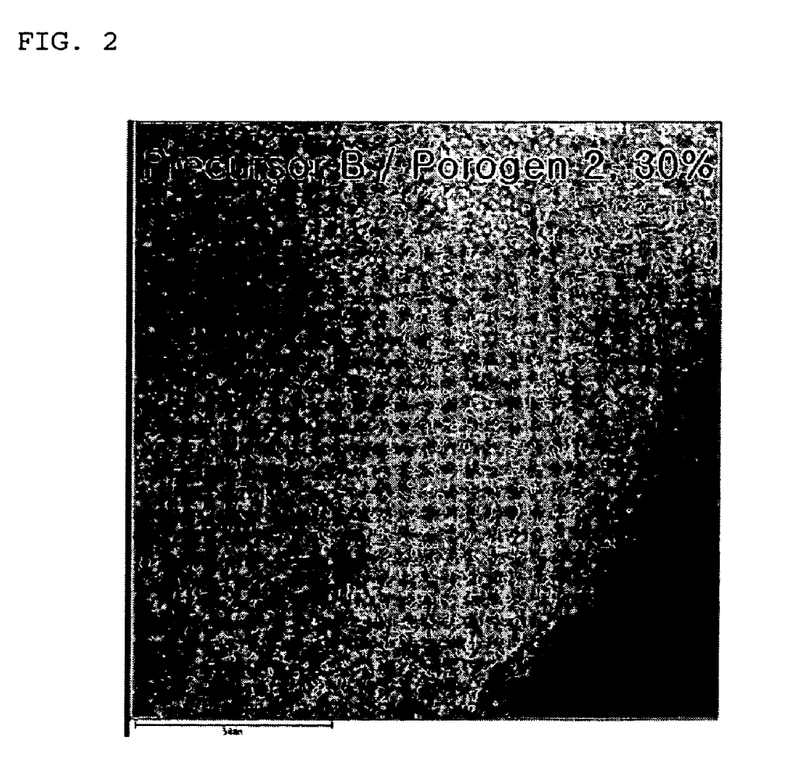
FIG. 2 is a sectional TEM image of a thin film formed using a composition prepared in Example 4-3 of the present invention.
Figure 3:
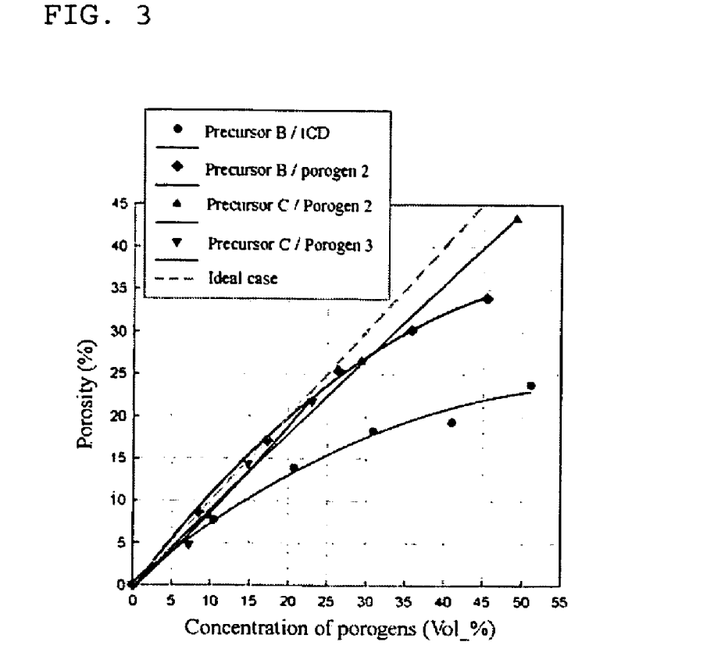
FIGS. 3 and 4 are graphs showing changes in the porosity of some thin films formed in Example 4 of the present invention with increasing concentrations of porogens used.
Figure 4:
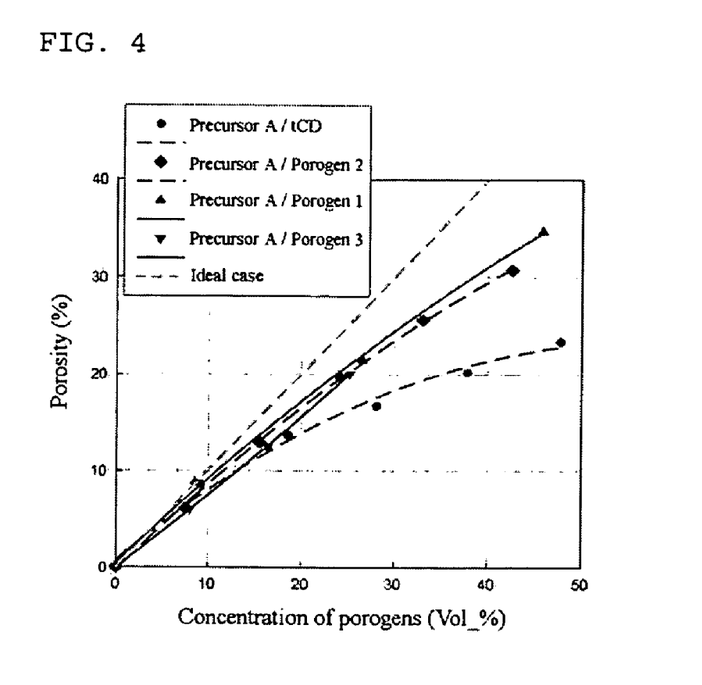
Figure 5:
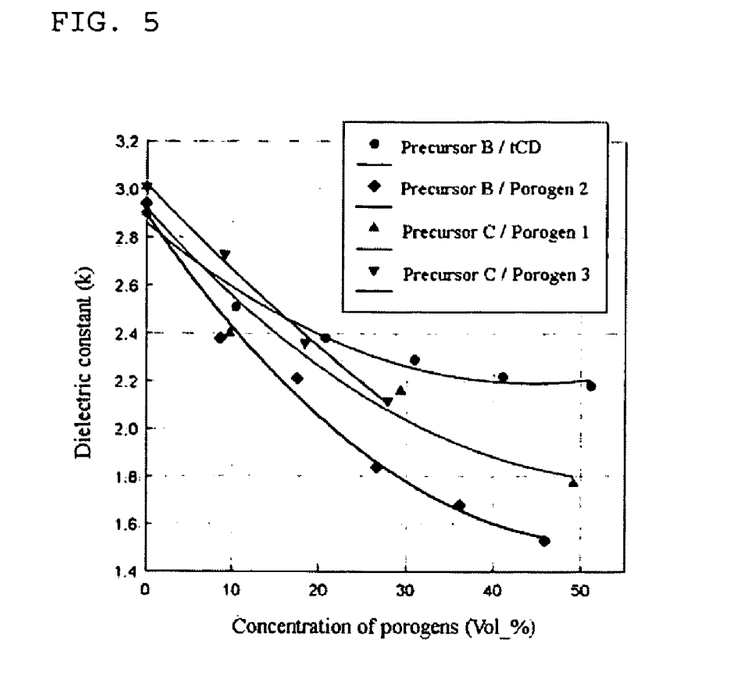
FIGS. 5 and 6 are graphs showing changes in the dielectric constant of some thin films formed in Example 4 of the present invention with increasing concentrations of porogens used.
Figure 6:
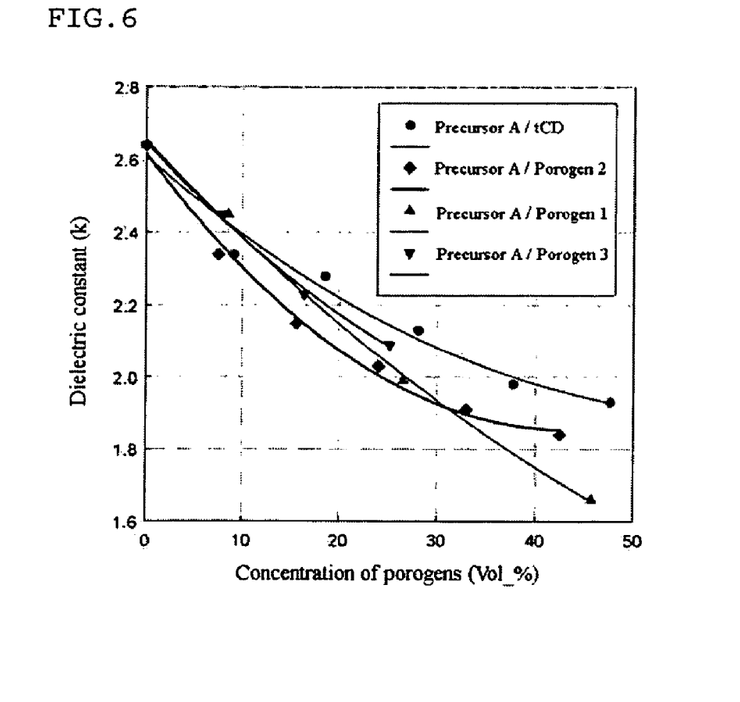

To observe whether nanopores were uniformly formed in the thin films or not, sectional images of the thin films were taken using TEM H9000NA at 300 kV. The sectional TEM image of the thin film formed using the composition prepared in Example 4-3 is shown in FIG. 2. Nanopores having a size of 50 Å or more, which results from agglomeration of porogens, were not found, and thus it could be confirmed from this observation that nanopores were uniformly formed in the thin films. The pore size (nm) was quantitatively measured by positron annihilation lifetime spectroscopy (PALS). The results are shown in Tables 4 and 5 below. Based on the results shown in Tables 4 and 5, graphs showing changes in the porosity of some thin films formed in Example 4 with increasing proportions of porogens were plotted (FIGS. 3 and 4). As can be seen from the results shown in FIGS. 3 and 4, as the porogen content increases, the porosity of the thin films formed using the compositions of the present invention constantly increases, when compared to that of the thin films formed using the compositions (comprising tCD(heptakis(2,3,6-tri-O-methyl)-β-cyclodextrin as a porogen) prepared in Comparative Examples. FIGS. 5 and 6 are graphs showing changes in the dielectric constant of some thin films formed in Example 4 with increasing concentrations of porogens used. It could be confirmed from the results shown in FIGS. 5 and 6 that in the case where the porogen concentration is high, the dielectric constant of the thin films formed using the compositions of the present invention is lower than that of the thin films formed using the compositions prepared in Comparative Examples.

TABLE 4

| Example No. | Solid content (precursor + porogen), wt % | Kind of precursors | Porogens Kind | Content (wt %) | Thickness (nm) | Refractive Index | Dielectric constant | Modulus (Gpa)[b] | Hardness (Gpa)[b] | Porosity (%)[a] | Pore size (nm) |
|---|---|---|---|---|---|---|---|---|---|---|---|
| Ex. 1-1 | 30 | A | 1 | 10 | 1225 | 1.3690 | 2.45 | 3.93 | 0.69 | 8.8 | 1.60 |
| Ex. 1-2 | 30 | A | 1 | 30 | 1225 | 1.3126 | 1.99 | 2.52 | 0.41 | 21.5 | 1.81 |
| Ex. 1-3 | 30 | A | 1 | 50 | 1118 | 1.2562 | 1.66 | 1.55 | 0.23 | 34.7 | 1.87 |
| Ex. 2-1 | 30 | A | 2 | 10 | 1482 | 1.3826 | 2.34 | 4.59 | 0.86 | 6.1 | 1.54 |
| Ex. 2-2 | 30 | A | 2 | 20 | 1393 | 1.3520 | 2.15 | 3.39 | 0.58 | 12.9 | 1.73 |
| Ex. 2-3 | 30 | A | 2 | 30 | 1378 | 1.3215 | 2.03 | 2.52 | 0.40 | 19.8 | 1.81 |
| Ex. 2-4 | 30 | A | 2 | 40 | 1379 | 1.2960 | 1.91 | 1.87 | 0.28 | 25.6 | 1.85 |
| Ex. 2-5 | 30 | A | 2 | 50 | 1074 | 1.2742 | 1.84 | 1.67 | 0.25 | 30.7 | 1.93 |
| Ex. 3-1 | 30 | A | 3 | 10 | 1682 | 1.3818 | 2.45 | 4.79 | 0.79 | 6.0 | 1.71 |
| Ex. 3-2 | 30 | A | 3 | 20 | 2047 | 1.3525 | 2.23 | 3.36 | 0.58 | 12.5 | 1.75 |
| Ex. 3-3 | 30 | A | 3 | 30 | 1416 | 1.3193 | 2.09 | 2.72 | 0.42 | 20.0 | 1.83 |
| Ex. 4-1 | 32 | B | 2 | 10 | 902 | 1.3380 | 2.38 | 6.30 | 1.02 | 8.7 | 1.54 |
| Ex. 4-2 | 32 | B | 2 | 20 | 919 | 1.3040 | 2.21 | 4.44 | 0.72 | 17.1 | 1.75 |
| Ex. 4-3 | 32 | B | 2 | 30 | 856 | 1.2711 | 1.84 | 3.12 | 0.48 | 25.4 | 1.88 |
| Ex. 4-4 | 32 | B | 2 | 40 | 893 | 1.2524 | 1.68 | 2.58 | 0.41 | 30.2 | 1.92 |
| Ex. 4-5 | 32 | B | 2 | 50 | 747 | 1.2377 | 1.53 | 2.40 | 0.37 | 34.0 | 1.97 |
| Ex. 5-1 | 32 | C | 1 | 10 | 1429 | 1.3466 | 2.40 | 7.07 | 1.25 | 8.02 | 1.45 |
| Ex. 5-2 | 32 | C | 1 | 30 | 1199 | 1.2718 | 2.16 | 4.37 | 0.74 | 26.5 | 1.68 |
| Ex. 5-3 | 32 | C | 1 | 50 | 1083 | 1.2063 | 1.77 | 2.81 | 0.45 | 43.3 | 1.78 |
| Ex. 6-1 | 32 | C | 3 | 10 | 1511 | 1.3610 | 2.73 | 7.23 | 1.22 | 4.8 | 1.54 |
| Ex. 6-2 | 32 | C | 3 | 20 | 1415 | 1.3224 | 2.36 | 5.02 | 0.79 | 14.0 | 1.68 |
| Ex. 6-3 | 32 | C | 3 | 30 | 1556 | 1.2909 | 2.12 | 3.26 | 0.50 | 21.8 | 1.75 |

TABLE 5

| Example No. | Solid content (precursor + porogen), wt % | Kind of precursors | Porogens Kind | Content (wt %) | Thickness (nm) | Refractive Index | Dielectric constant | Modulus (Gpa)[b] | Hardness (Gpa)[b] | Porosity (%)[a] | Pore size (nm) |
|---|---|---|---|---|---|---|---|---|---|---|---|
| Comp. Ex. 1 | 30 | A | — | — | 1429 | 1.4093 | 2.64 | 6.12 | 1.21 | 0.0 | 0.60 |
| Comp. Ex. 2-1 | 30 | A | tCD | 10 | 1468 | 1.3698 | 2.34 | 4.42 | 0.90 | 8.6 | 1.44 |
| Comp. Ex. 2-2 | 30 | A | tCD | 20 | 1337 | 1.3471 | 2.28 | 3.68 | 0.75 | 13.7 | 1.71 |
| Comp. Ex. 2-3 | 30 | A | tCD | 30 | 1175 | 1.3335 | 2.13 | 3.36 | 0.59 | 16.7 | 1.80 |

TABLE 5-continued

| Example No. | Solid content (precursor + porogen), wt % | Kind of precursors | Porogens Kind | Content (wt %) | Thickness (nm) | Refractive Index | Dielectric constant | Modulus (Gpa)[b] | Hardness (Gpa)[b] | Porosity (%)[a] | Pore size (nm) |
|---|---|---|---|---|---|---|---|---|---|---|---|
| Comp. Ex. 2-4 | 30 | A | tCD | 40 | 1174 | 1.3184 | 1.98 | 2.67 | 0.53 | 20.2 | 1.98 |
| Comp. Ex. 2-5 | 30 | A | tCD | 50 | 1037 | 1.3045 | 1.93 | 2.50 | 0.48 | 23.4 | 2.10 |
| Comp. Ex. 3 | 32 | B | — | — | 1260 | 1.3788 | 2.94 | 7.88 | 1.45 | 0.0 | 0.60 |
| Comp. Ex. 4-1 | 32 | B | tCD | 10 | 1285 | 1.3463 | 2.51 | 6.45 | 1.18 | 7.73 | 1.45 |
| Comp. Ex. 4-2 | 32 | B | tCD | 20 | 1193 | 1.3210 | 2.38 | 5.33 | 0.94 | 13.9 | 1.54 |
| Comp. Ex. 4-3 | 32 | B | tCD | 30 | 1144 | 1.3031 | 2.29 | 4.68 | 0.81 | 18.3 | 1.71 |
| Comp. Ex. 4-4 | 32 | B | tCD | 40 | 1417 | 1.2987 | 2.22 | 3.89 | 0.68 | 19.4 | 1.76 |
| Comp. Ex. 4-5 | 32 | B | tCD | 50 | 942 | 1.2808 | 2.18 | 3.55 | 0.65 | 23.8 | 1.78 |
| Comp. Ex. 5 | 32 | C | — | — | 1112 | 1.3820 | 3.01 | 8.99 | 1.56 | 0.0 | 0.60 |

As apparent from the above description, although the composition of the present invention is used in a small amount, nanoporous materials containing optimized pores can be prepared from the composition. Further, thin films having superior mechanical properties relative to the same dielectric constant can be formed.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A cyclodextrin derivative represented by Formula 8 below:

(8)

wherein n is an integer from 6 to 10; $R_1'$ and $R_2'$ are independently a divalent group derived from substituents containing OH, SH or $NH_2$ which form a crosslinked structure; and $R_3$ is —$OR_4$, wherein $R_4$ is a $C_{2-30}$ acyl group, a $C_{1-20}$ alkyl group, a $C_{3-10}$ cycloalkyl group, a $C_{1-20}$ hydroxyalkyl group, a carboxyl group, or a silicon compound represented by $Sir_1r_2r_3$, wherein $r_1$, $r_2$ and $r_3$ are independently a $C_{1-5}$ alkyl group, a $C_{1-5}$ alkoxy group, or a $C_{6-20}$ aryl group.

2. A composition for preparing a nanoporous material, comprising:

i) at least one cyclodextrin derivative selected from compounds represented by Formula 8 below:

(8)

wherein n is an integer of from 6 to 10; $R_1'$ and $R_2'$ are independently a divalent group derived from substituents containing OH, SH or $NH_2$ which form a crosslinked structure; and $R_3$ is —$OR_4$ wherein $R_4$ is a $C_{2-30}$ acyl group, a $C_{1-20}$ alkyl group, a $C_{3-10}$ cycloalkyl group, a $C_{1-20}$ hydroxyalkyl group, a carboxyl group, or a silicon compound represented by $Sir_1r_2r_3$,wherein $r_1$, $r_2$ and $r_3$ are independently a $C_{1-5}$ alkyl group, a $C_{1-5}$ alkoxy group, or a $C_{6-20}$ aryl group; and (9)

wherein n is an integer of from 3 to 10; $R_3'$ is a divalent group derived from substituents containing OH, SH or $NH_2$ which form a crosslinked structure; and $R_1$ and $R_2$ are independently —OR$_4$ [in which R$_4$ is a C$_{2\sim30}$ acyl group, a C$_{1\sim20}$ alkyl group, a C$_{3\sim10}$ cycloalkyl group, a C$_{1\sim20}$ hydroxyalkyl group, a carboxyl group, or a silicon compound represented by Sir$_1$r$_2$r$_3$ (in which r$_1$, r$_2$ and r$_3$ are independently a C$_{1\sim5}$ alkyl group, a C$_{1\sim5}$ alkoxy group, or a C$_{6\sim20}$ aryl group)];

ii) a thermostable matrix precursor; and iii) a solvent for dissolving the components i) and ii).

3. The composition according to claim 2, wherein the thermostable matrix precursor is a siloxane-based resin prepared through hydrolysis and condensation of a compound represented by Formula 1 below:

(1)

wherein R$_1$ is a hydrogen atom, a C$_{1\sim3}$ alkyl group, or a C$_{6\sim15}$ aryl group; X$_1$, X$_2$ and X$_3$ are independently a hydrogen atom, a C$_{1\sim3}$ alkyl group, a C$_{1\sim10}$ alkoxy group, or a halogen atom, at least one of these substituents being a hydrolysable functional group; m is an integer ranging from 0 to 10; and p is an integer ranging from 3 to 8, or Formula 2 below:

(2)

wherein R$_1$ is a hydrogen atom, a C$_{1\sim3}$ alkyl group, or a C$_{6\sim15}$ aryl group; R$_2$ is a hydrogen atom, a C$_{1\sim10}$ alkyl group, or SiX$_1$X$_2$X$_3$, wherein X$_1$, X$_2$ and X$_3$ are independently a hydrogen atom, a C$_{1\sim3}$ alkyl group, a C$_{1\sim10}$ alkoxy group, or a halogen atom and p is an integer between 3 and 8, and a monomer represented by Formula 5 below:

$$RSiX_1X_2X_3 \quad (5)$$

wherein R is a hydrogen atom, a C$_{1\sim3}$ alkyl group, a C$_{3\sim10}$ cycloalkyl group, a C$_{1\sim10}$ alkoxy group, or C$_{6\sim15}$ aryl group; and X$_1$, X$_2$ and X$_3$ are independently a C$_{1\sim3}$ alkyl group, a C$_{1\sim10}$ alkoxy group, or a halogen atom, using an acid catalyst and water in the presence of an organic solvent.

4. The composition according to claim 3, wherein the compound of Formula 1 or 2 and the monomer of Formula 5 are used in a molar ratio ranging from 0.01:0.99 to 0.99:0.01.

5. The composition according to claim 2, wherein the content of the cyclodextrin derivative is in the range of 0.1%~95% by weight, based on the total solid content, the sum of the amounts of the cyclodextrin derivative and the matrix precursor, of the composition.

6. The composition according to claim 2, wherein the content of the solvent in the composition is in the range of 20%~99.9% by weight.

7. The composition according to claim 2, wherein the solvent is an aromatic hydrocarbon, a ketone, an ether, an acetate, an amide, γ-butyolactone, an alcohol, a silicon solvents, or a mixture thereof.

8. The composition according to claim 7, wherein the solvent is anisole, xylene, mesitylene, methyl isobutyl ketone, 1-methyl-2-pyrrolidinone, acetone, tetrahydrofuran, isopropyl ether, ethyl acetate, butyl acetate, propylene glycol methyl ether acetate, dimethylacetamide, dimethylformamide, γ-butyolactone, isopropyl alcohol, butyl alcohol, octyl alcohol, a silicon solvent, or a mixture thereof.

9. A method for forming a low dielectric constant film, comprising the steps of: coating the composition according to claim 2 on a semiconductor substrate by spin coating, dip coating, spray coating, flow coating, or screen printing; evaporating the solvent from the coated substrate; and heating the coated substrate to 150° C.~600° C. under an inert atmosphere or vacuum.

10. A nanoporous structure produced by preparing the composition according to claim 2 and evaporating the solvent from said composition—therefor.

11. A method for the manufacture of heat resistant materials, electrical insulators, adsorbents, and supports for catalysts, the method comprising the preparation of the composition of claim 3 and evaporating the solvent from said composition—therefore.

* * * * *